(12) United States Patent
Catterson et al.

(10) Patent No.: US 11,379,757 B2
(45) Date of Patent: Jul. 5, 2022

(54) METHODS, SYSTEMS, AND FRAMEWORKS FOR DATA ANALYTICS USING MACHINE LEARNING

(71) Applicant: BioSymetrics, Inc., New York, NY (US)

(72) Inventors: Victoria Catterson, Toronto (CA); Babak Afshin-Pour, Oakville (CA); Cindy Lopes, Toronto (CA); Jill Cates, Burlington (CA); Anthony Iacovone, Huntington, NY (US); Gabriel Musso, Toronto (CA)

(73) Assignee: BioSymetrics, Inc., New York, NY (US)

( * ) Notice: Subject to any disclaimer, the term of this patent is extended or adjusted under 35 U.S.C. 154(b) by 265 days.

(21) Appl. No.: 16/528,497

(22) Filed: Jul. 31, 2019

(65) Prior Publication Data
US 2021/0035017 A1 Feb. 4, 2021

(51) Int. Cl.
*G06N 20/00* (2019.01)
*G16H 30/20* (2018.01)

(52) U.S. Cl.
CPC ............ *G06N 20/00* (2019.01); *G16H 30/20* (2018.01)

(58) Field of Classification Search
CPC .............................. G06N 20/00; G16H 30/20
See application file for complete search history.

(56) References Cited

U.S. PATENT DOCUMENTS

| | | | |
|---|---|---|---|
| 2019/0272890 A1* | 9/2019 | Aliper | G16B 40/00 |
| 2020/0098443 A1* | 3/2020 | Frenkel | G16B 45/00 |
| 2020/0327404 A1* | 10/2020 | Miotto | G16H 50/70 |

* cited by examiner

*Primary Examiner* — Thai Q Tran
*Assistant Examiner* — Jose M Mesa

(57) ABSTRACT

Some embodiments relate to methods, systems, and frameworks for data analytics using machine learning, such as methods and systems for preprocessing of biomedical data, using machine learning, for input to a predictive model. The method may include receiving data from a data source, using at least one machine learning (ML) algorithm from a plurality of ML algorithms to obtain at least one combination of preprocessing steps, and computing an accuracy score for each of the at least one combination based on accuracy of prediction of the predictive model. The method may further include using at least one ML algorithm to optimize the feature selection of the predictive model, combining a plurality of datasets into a single dataset, and using a parallel computing network to provide a framework for executing such predictive model.

21 Claims, 11 Drawing Sheets

METHODS, SYSTEMS, AND FRAMEWORKS FOR DATA ANALYTICS USING MACHINE LEARNING

BACKGROUND

Some embodiments generally relate to methods, systems, and frameworks for data analytics using machine learning. In particular, some embodiments relate to preprocessing biomedical data, using machine learning, such as for input to a predictive model.

The availability of biomedical data is at an all-time high due to breakthroughs made in the fields of genomics, proteomics, medical imaging, and wearable medical devices. For example, the cost of human genome sequencing has decreased tremendously from $3 billion in 2003 to $5,000 per genome in 2013. As a result, the approach for treatment of diseases has changed significantly to become heavily data driven. Data collection methods are becoming increasingly digital and automated. Precision medicine (a system for more personalized disease treatment) and robot-assisted surgeries are now a reality.

Breakthroughs have also been made in the fields of data science, machine learning, artificial intelligence, and computer processing. These fields have been applied successfully to automate data analysis of large datasets, also known as big data. In biomedical data too, these approaches have been applied successfully. However, the rapid increase in data has made it essential for the data processing technologies to keep evolving with the challenges of big data. Efforts are also being made to improve the performance of such automated analysis in terms of speed of computation as well as accuracy of analysis.

Data pre-processing is one of the initial stages in a data analysis method involving making the raw data more consistent and transforming it into a form that can be used for optimized analytic outcome. Data preprocessing often involves some computer programming and mathematics which a biomedical scientist may not have competency with. Feature selection is also a step in a data analysis method, involving selecting certain variables which directly impact the outcome of a model (for example diagnosis of a disease). However, in large dataset(s), with numerous variables, it may be a difficult procedure to execute. Integration of datasets leads to a larger set of variables and may increase the reliability of predictions of a model. Optimizing the analysis of biomedical phenomenon (e.g., diagnostics, therapeutics, drug discovery, classifying different biological components, interpreting experimental results from model organisms), may require the use of different datasets along with distinct types of preprocessing and feature selection strategies so that the successful integration and analysis of the datasets may involve examining many different variables. Cloud-based as well as multi-processor equipped hardware allows the execution of an algorithm in parallel over different Central Processing Units (CPUs) and/or Graphical Processing Units (GPU) as well as Tensor Processing Units (developed by Google), Programmable Gate Arrays (PGA), Digital Signal Processors (DSP) and other processing technologies, leading to a higher computational capacity. Despite these innovations in computation, running different data pre-processing routings to achieve the best results often requires substantial compute resources which can consume substantial time and/or monies when fee-based computation is used (e.g., with many fee-based or compute-usage based, cloud-based computing resources).

SUMMARY

It may therefore be advantageous to address one or more of the issues identified above, such as by using a system to automate and optimize a preprocessing algorithm in a predictive model. The ML algorithm allows the selection of a suitable combination of preprocessing steps, with each of the preprocessing steps in the combination having suitable associated parameters, for a particular data type.

It may also be advantageous to address one or more of the issues identified above, such as by using an ML algorithm to obtain a plurality of features to successfully make use of a dataset. The ML algorithm tests each of the features of the dataset for their impact on the prediction accuracy and gives a set of relevant and optimized features for the predictive model.

It may also be advantageous to address one or more of the issues identified above, such as by combining a plurality of datasets of varying data types into a single dataset and using an ML algorithm to perform preprocessing and feature selection on the combined data set. The ML algorithm provides means by which the evaluation of the various combinations of datasets and a set of features from the combined dataset can be conducted to optimize the predictive value of the data.

It may also be advantageous to address one or more of the issues identified above, such as by using a parallel computing network to run the preprocessing, feature selection, and data integration algorithms. The parallel computing network provides additional CPUs and/or GPUs and a framework for a plurality of users to work on the same dataset.

Some embodiments therefore provide method and system for preprocessing, feature selection and integration of data that may be deployed over a cloud network.

One such embodiment is a method for preprocessing biomedical data for a predictive model. The method includes receiving data from a data source. The method further includes using at least one ML algorithm from a plurality of ML algorithms to obtain at least one combination of preprocessing steps. The method further includes computing an accuracy score for each of the at least one combination based on accuracy of prediction of the predictive model.

Another such embodiment is a preprocessing device for preprocessing biomedical data for a predictive model. The preprocessing device includes at least one processor and a computer-readable medium storing instruction that, when executed by at least one processor, causes at least one processor to perform operations. The device includes receiving data from a data source. The device further includes using at least one ML algorithm from a plurality of ML algorithms to obtain at least one combination of preprocessing steps. The device includes computing an accuracy score for each of the at least one combination based on accuracy of prediction of the predictive model.

Yet another such embodiment is a method of selecting features from biomedical data for a predictive model. The method includes receiving data from a data source. The method further includes generating a number of features to be used for a predictive analysis of the data, wherein a feature is a random variable having an impact on an outcome of the predictive model. The method further includes iterating over a range of features to select a suitable number of features for the predictive model. The method further includes using a transformation algorithm to convert the selected features into different mathematical functions of the selected features.

Yet another such embodiment is a method of combining a plurality of biomedical datasets for a predictive model. The method includes receiving a query from a user for a plurality of datasets to be combined. The method further includes receiving the plurality datasets to be combined from at least one data source. The method further includes combining the plurality of datasets.

Yet another embodiment is a method of using a computing network to run a predictive model for biomedical data. The method includes receiving data from a data source through an Application Programming Interface (API), wherein the API is a framework to allow the parallel computing network access to the data source. The method further includes storing a part of the data received from the data source through the API as a cache memory. The method further includes storing a list of a plurality of tasks in a task queue, wherein the plurality of tasks is performed in the background of the parallel computing network. The method further includes allowing a plurality of users to work together on the data. The method further includes distributing a plurality of algorithms over a plurality of CPUs.

The techniques of the above embodiments provide for an ML framework for analyzing biomedical data using a predictive model. The techniques may use ML itself for optimizing each step of the predictive model. The techniques further seek to reduce the compute resource, in particular, processor utilization, thereby making the process of data analytics compatible with cost-structure which is frequently associated with cloud-based computing. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

(1) Summaries of Various Embodiments

One or more embodiments of preprocessing biomedical data for a predictive model are disclosed. The one or more embodiments provide for an ML framework for analyzing biomedical data using a predictive model. The one or more embodiments make use of the various components including preprocessing, feature selection, data integration, and parallel computing network.

(1.1) Preprocessing

Preprocessing is a method for preparing a data, in its raw form, for further data analysis in a predictive model. Raw data may not be in a suitable format and may also contain biases due to differences in equipment, variations in equipment use, or variations in reporting of data. Data in the form of images, for example, needs to be converted to a matrix form for data analysis. Preprocessing also ensures that data biases do not lead to faulty predictions by detecting and correcting them. Different datasets have different preprocessing requirements and each of the steps of a preprocessing algorithm may have a plurality of parameters.

(1.2) Feature Selection

Features are variables on which the outcome or the result of the analysis is dependent. In a data, a lot of variables may be present. Using all of these in analysis may give misleading results for a predictive model. Feature selection is a process which performs the selection of relevant variables so as to enhance the accuracy of the predictive model.

(1.3) Data Integration

Data integration is the process of combining a plurality of datasets into a single dataset for data analysis. Each of the plurality of datasets may have different preprocessing needs but the combined dataset will have all the features of each of the plurality of datasets. Consequently, it will lead to high accuracy predictions and a reliable predictive model.

(1.4) Parallel Computing Network

A parallel computing network consists of a plurality of Central Processing Units (CPUs) working in parallel to provide an enhanced computational capability for the computational task allotted to the network. A parallel computing network may also allow multiple users working on a common task, thereby increasing productivity and efficiency of a workplace.

(2) Exemplary Environments to Employ Various Embodiments

Figure 1:
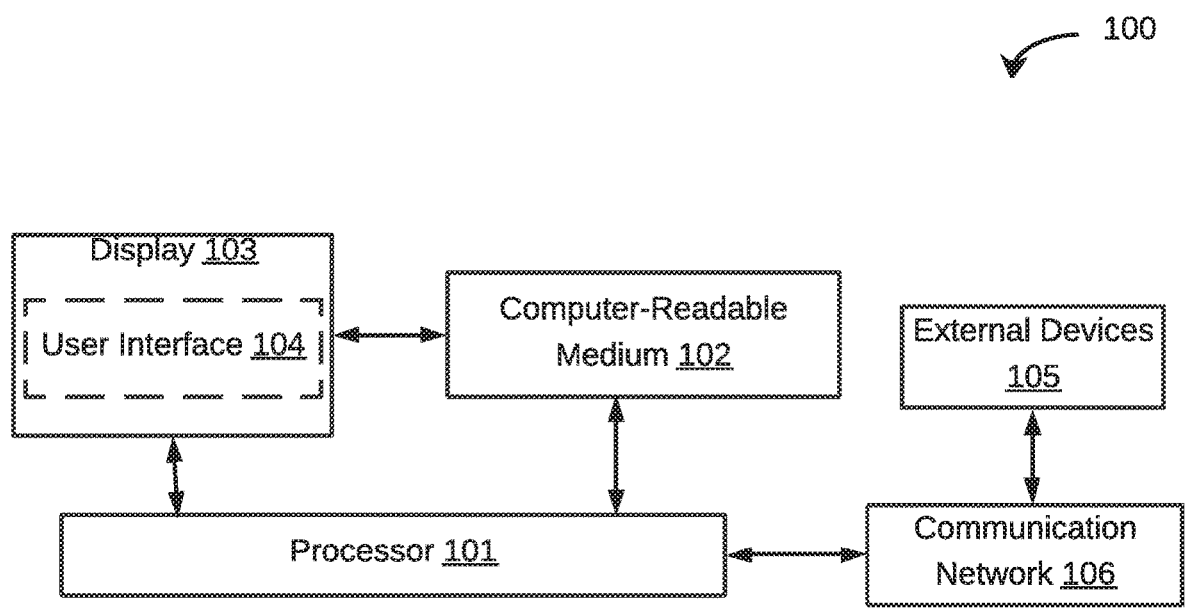
FIG. 1 is a block diagram of an exemplary system for preprocessing biomedical data, in accordance with some embodiments of the present disclosure.

Referring now to FIG. 1, an exemplary system 100 for preprocessing a biomedical data is illustrated, in accordance with some embodiments of the present disclosure. The system 100 may implement a preprocessing engine, in accordance with some embodiments of the present disclosure. In particular, the system 100 may include a preprocessing device (for example, server, desktop, laptop, notebook, netbook, tablet, smartphone, mobile phone, or any other computing device) that may implement the preprocessing engine. The preprocessing engine may preprocess the biomedical data using a machine learning (ML) algorithm.

The system 100 may include one or more processors 101, a computer-readable medium (for example, a memory) 102, and a display 103. The computer-readable storage medium 102 may store instructions that, when executed by the one or more processors 101, cause the one or more processors 101 to preprocess the biomedical data, in accordance with aspects of the present disclosure. The computer-readable storage medium 102 may also store various data that may be captured, processed, and/or required by the system 100. The system 100 may interact with a user via a user interface 104 accessible via the display 103. The system 100 may also interact with one or more external devices 105 over a communication network 106 for sending or receiving various data. The external devices 105 may include, but may not be limited to, a remote server, a digital device, or another computing system.

(3) Exemplary Systems for Various Embodiments

Figure 2A:
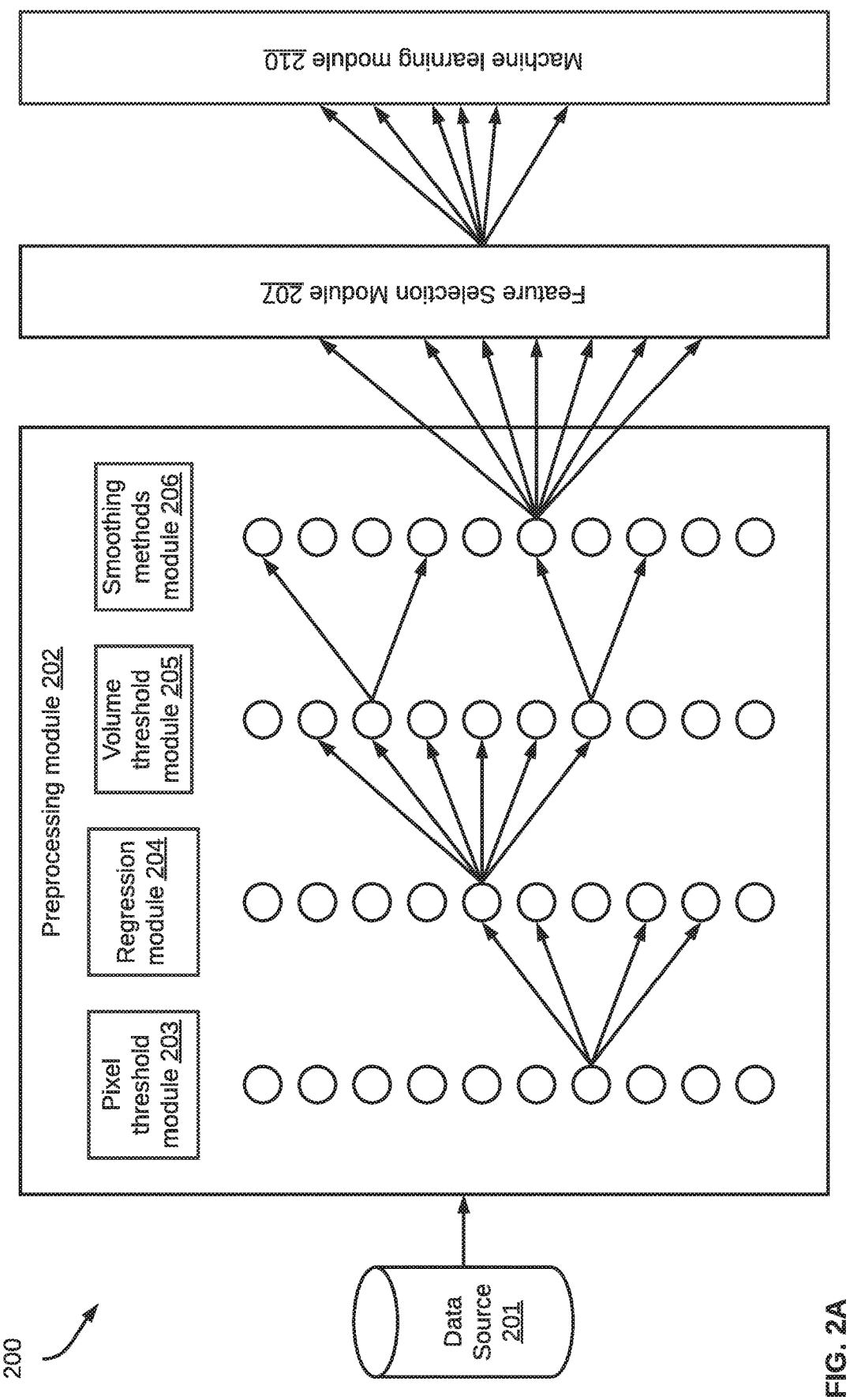
FIGS. 2A-C depict a block diagram of a machine learning (ML) framework, in accordance with some embodiments of the present disclosure.
Figure 2B:
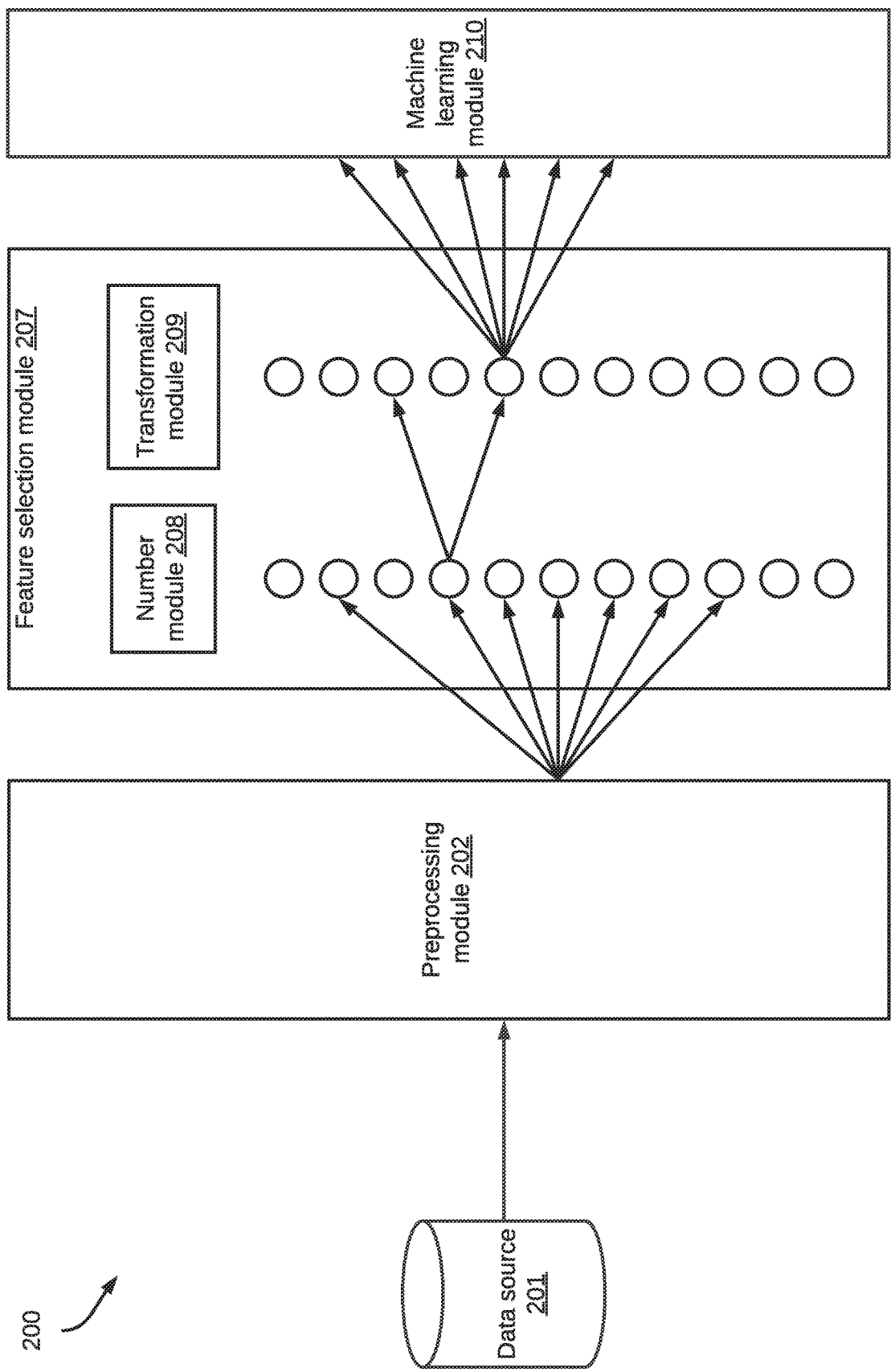
Figure 2C:
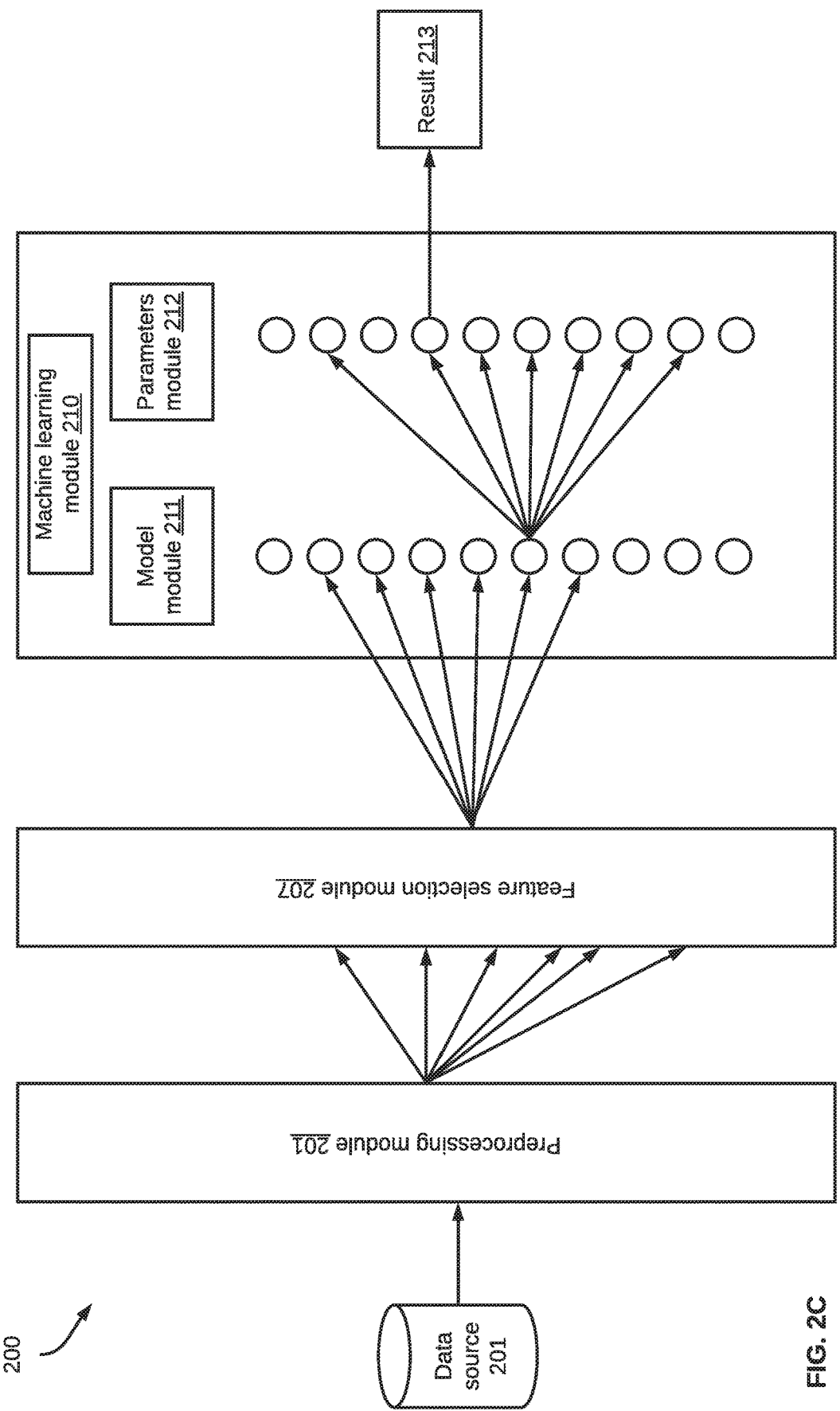

Referring now to FIGS. 2A-C, a block diagram of an ML framework 400 implemented by the system 100, is illustrated, in accordance with some embodiments of the present disclosure. The ML framework 200 includes a data source 201, a preprocessing module 202, a feature selection module 207, and an ML module 210.

The data source 201 is a system for storage of a data and provides an input data to the preprocessing module 202. Some examples include, but may not be limited to, a local storage data, a database, or a cloud storage data. There may be more than one data sources for the ML framework 200.

The preprocessing module 202 includes a pixel threshold module 203, a regression module 204, a volume threshold module 205, and a smoothing methods module 206. The preprocessing module 202 receives the input data and returns a preprocessed input data as an output.

The pixel threshold module 203 uses a pixel thresholding algorithm on the input data, wherein the input data is an image. The pixel thresholding algorithm simplifies the input data for analytical purposes. The parameters for a pixel thresholding algorithm may be an intensity of each of pixels of an image or a color of each of the pixels of the image.

The regression module 204 uses a regression algorithm to perform preprocessing of the input data. The regression algorithm may be a linear or a non-linear regression algorithm. The preprocessing of the input data may be in the form of a transformation of the input data, a reduction in the outliers of the input data, a thresholding of the input data, a normalization of the input data, any other conventional preprocessing techniques, or any preprocessing technique yet to be discovered.

The volume threshold module 205 uses a volume thresholding algorithm on the input data, wherein the input data is a 3-dimensional (3D) image such as MRI or CT scan, or microscopy image. The volume thresholding algorithm simplifies the input data for a volumetric analysis, wherein the volumetric analysis may be used for estimating a volume of a region (for example, a hypothalamus region of a human brain in an MRI image) from the 3D image. The parameters for a volume thresholding algorithm may include a threshold for reduction of noise in the input data and a 3-dimensional region to be analyzed.

The smoothing methods module 206 uses at least one smoothing method to simplify and generalize the input data. The smoothing methods may include, but may not be limited to, an additive smoothing algorithm, an exponential smoothing algorithm, a kernel smoother, a Laplacian smoothing algorithm, and any other data smoothing or data filtering algorithm. The use of a particular smoothing method depends on the type and distribution of the input data.

The feature selection module 207 includes a number module 208 and a transformation module 209. The feature selection module 207 receives an input data from the preprocessing module 202 and returns a set of features relevant for the predictive analysis of the predictive model.

The number module 208 generates a number of features to be used for the predictive analysis of the input data, wherein a feature is a random variable having an impact on an outcome of the predictive model. The feature selection module 207 may iterate over a range of two given numbers of features to select a suitable number of features for the predictive model.

Once the number of features is generated, the transformation module 209 then uses a transformation algorithm such as a principal component analysis (PCA), independent component analysis (ICA), or any other linear or non-linear feature transformation algorithms. The transformation algorithm converts the selected features into different functions of the selected features. A linear transformation algorithm maintains the linear relationships of a feature with other features whereas a nonlinear transformation algorithm changes the linear relationships of a feature with other features. The transformation module 209 may iterate over different transformation algorithms and their associated parameters to select a suitable transformation algorithm and a suitable set of associated parameters for the predictive model.

The ML module 210 includes a model module 211 and a parameters module 212. The ML module 210 uses an ML algorithm to perform a predictive analysis using the preprocessed data obtained from the preprocessing module 202 and the features obtained from the feature selection module 207. The predictive analysis may be, but may not be limited to, diagnosis of a disease, prediction of a probability of getting a disease, and determining an optimum treatment course for a more personalized and high precision medicine course. The ML module 210 gives a result 213 as an output. The result 213 includes the predictions of the ML framework 200 based on the input data received from the data source 201. The result 213 may be visualized using any of the standard data visualization packages such as Seaborn or Matplotlib.

The model module 211 selects a suitable predictive model, based on the data type of the input data, for performing the predictive analysis using the input data. The suitable predictive model may be a support vector machine (SVM) model, a random forest (RF) model, a neural network (NN) model, or any other ML model or a deep learning model, or a combination thereof. The model module 211 receives the preprocessed data (from the preprocessing module 202) and the features (from the feature selection module 207) as an input and generates the suitable predictive model for predictive analysis. In another embodiment, the suitable predictive model may be generated as a result of iterations performed by a second ML algorithm within the ML module 210 to determine a suitable predictive model for the input data.

The parameters module 212 iterates over a set of parameters for the predictive model generated by the model module 211 to generate a suitable value for each of the predictive model parameters. The predictive model parameters depend upon the type of the predictive model generated. For example, for an RF model, one of the predictive model parameters may be a number of decision trees, wherein each of the decision trees is a classification model, whereas for an SVM model, one of the predictive model parameters may be a type of a kernel, wherein the kernel is a set of mathematical functions for generalizing a non-linear classification problem. The parameter values may then be used to generate an ML algorithm for performing predictive analysis.

(4) Reducing Computational Time by Way of Using Parallel Computing Network

Figure 3:
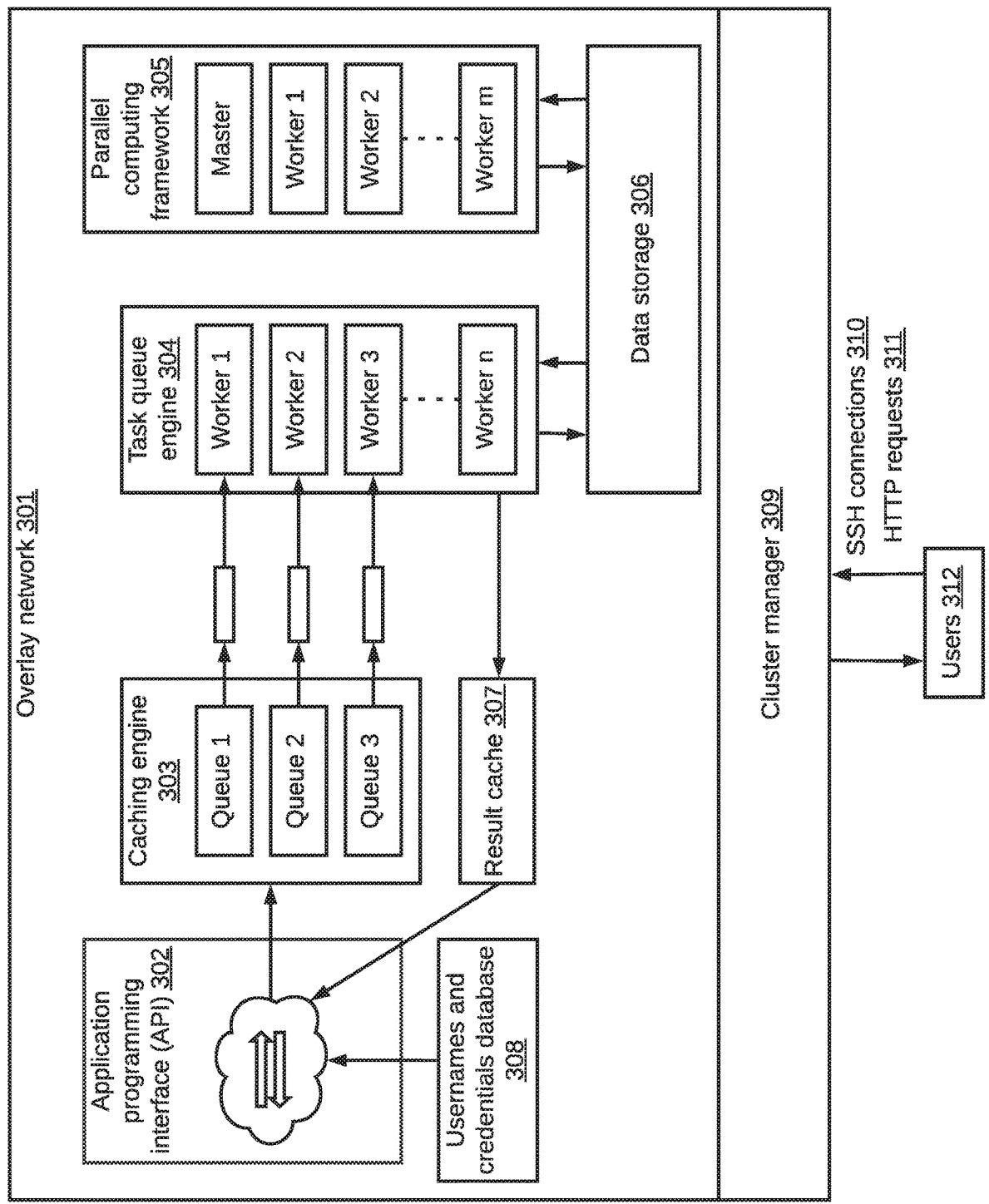
FIG. 3 is a block diagram of the ML framework of FIGS. 2A-C functioning over a parallel computing network, in accordance with some embodiments of the present disclosure.

Referring now to FIG. 3, a block diagram of the ML framework 200 of FIGS. 2A-C functioning over a parallel computing network 300, implemented by the system 100 of FIG. 1, is illustrated, in accordance with some embodiments of the present disclosure. The parallel computing network 300 includes an overlay network 301 and a cluster manager 309.

The overlay network 301 includes an application programming interface (API) 302, a caching engine 303, a task queue engine 304, a parallel computing framework 305, and a data storage 306. The overlay network 301 is a framework for enabling parallel computing for a plurality of users 312.

The API 302 is a framework to allow the parallel computing network 300, access to the data source 201. As new data entries keep adding to the data source 201, the API 302 updates continuously after a particular time interval such that the parallel computing network 300 gets access to an updated data from the data source 201. The API 302 also allows the parallel computing network 300 access to a usernames and credentials database 308, wherein the usernames and credentials of a plurality of users, such as a plurality of employees or freelancers, may be stored. A results cache 307 is received by the API 302, wherein the results cache 307 is an access layer for a result obtained by one user allowing a faster access to the result for the other users.

The caching engine 303 is a data storage in a fast access memory hardware such as a Random Access Memory (RAM). When a data is retrieved from the data source 201 for the first time, a part of its information is stored as a cache in the caching engine 303. When the data is accessed for a successive time, the cache speeds up the data access for the users 312. The caching engine 303 may be based on Redis or any other data structure capable of running as a cache framework.

The task queue engine 304 is a data structure containing a list of tasks to be performed in the background. The tasks may be, retrieval of an updated data from the data source 201 or retrieval of results from the data storage 306. If the data from the data source 201 has been previously retrieved, the caching engine 303 allows a faster access to the data source 201 for the task queue engine 304. The task queue engine 504 may be based on Celery or any other task queue framework.

The parallel computing framework 305 is a framework to allow a plurality of users 312 to work together on a common input data. The parallel computing framework 305 also allows a containerized deployment of algorithms for a faster execution of the preprocessing, the feature selection, the predictive model, and an integration of multiple data types, wherein the integration of multiple data types is combining a plurality of datasets into a common dataset to obtain an increased set of features and a higher accuracy. The containerized deployment includes a plurality of containers or modules, each of which is deployed with at least one algorithm to execute. Each container may package an application together with libraries and other dependencies to provide isolated environments for running the application. The parallel computing framework 305 may be based on Apache Spark or any other parallel computing platform. The data and results obtained by the parallel computing framework 305 are stored in the data storage 306.

The data storage 306 is primarily accessible by the users 312. The data storage 306 is a relatively local data storage when compared to the data source 201. It may include the data received from the parallel computing framework 305 and the data received from the data source 201 via the task queue engine 304.

The cluster manager 309 receives a user query from at least one user 312 via a Secure Shell (SSH) connection 310 or a Hyper Text Transfer Protocol (HTTP) request 311 and sends the user query to the overlay network 301. The cluster manager 309 also receives an output from the overlay network 301 and sends the output to each of the users 312 via the SSH connection 310 or the HTTP request 311.

(5) Iterative Preprocessing Input Data

Figure 4:
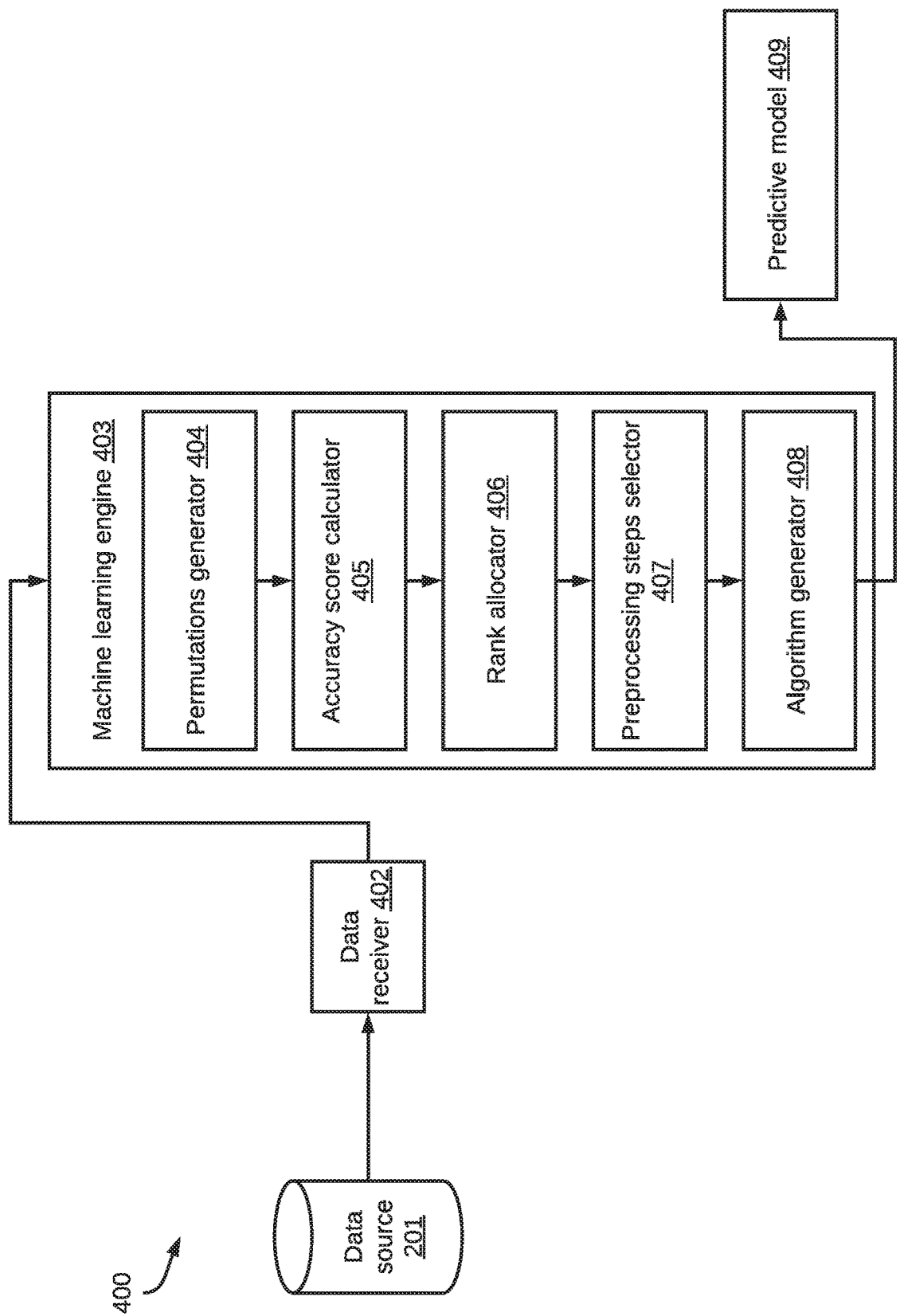
FIG. 4 is a block diagram of a preprocessing engine, in accordance with some embodiments of the present disclosure.

Referring now to FIG. 4, a block diagram of a preprocessing engine 400, implemented by the system 100 of FIG. 1, is illustrated, in accordance with some embodiments of the present disclosure. The preprocessing engine 400 includes a data source 201, a data receiver 402, an ML engine 403, and a predictive model 409.

The data source 201 is a system for storage of a data and provides an input data to the ML engine 403. Some examples include, but may not be limited to, a local storage data, a database, or a cloud storage data. The data receiver 402 receives the input data and identifies a data type of the input data. The input data is then transferred by the data receiver 402 to the ML engine 403.

The ML engine 403 further includes a preprocessing steps predictor 404, an accuracy score calculator 405, a rank allocator 406, a preprocessing steps selector 407, and an algorithm generator 408. The ML engine 403 contains a plurality of ML algorithms for different data types. The data receiver 402 identifies the data type of the input data and sends the information to the ML engine 403. One or more than one suitable ML algorithms can then be applied on various preprocessing parameters, based on the data type of the input data, to generate a specific and suitable preprocessing algorithm for the input data. The data types may include, but may not be limited to, Magnetic Resonance Imaging (MRI), functional Magnetic Resonance Imaging (fMRI) data, an Electroencephalogram (EEG) data, an Electrocardiogram (EKG/ECG) data, a genetics data, a proteomics data, data from wearable devices, an Electronic Health Record (EHR) data, and Electronic Medical Record (EMR) data, Chemical Structures (SMILES, InCHI, SDF), Images (PNG, JPEG), including from pathology or other applications of microscopy, and other healthcare and medical research related data options. The preprocessing parameters may include, but may not be limited to, a pixel threshold, a linear/nonlinear regression, a volume threshold, and a smoothing method.

The preprocessing steps predictor 404 uses the ML algorithm to identify the data type and generate various permutations of the preprocessing parameters. These permutations are then applied on a test data (a subset of the input data) to check for their respective prediction accuracy scores by the accuracy score calculator 405. The accuracy score may be classification accuracy, logarithmic loss, confusion matrix, area under curve, F1 score, mean absolute error, mean squared error, or any other performance evaluation metric.

Classification accuracy is the ratio of number of correct predictions to the total number of predictions made. It can be represented as per equation (1) below:

Accuracy=Correct/Total, - (1)

where Correct=number of correct predictions made
Total=total number of predictions made
Logarithmic loss penalizes false classifications and can be represented as per equation (2) below:

$$\text{Log loss} = \frac{-1}{N}\left(\sum_{i=1}^{N}\sum_{j=1}^{M} y_{ij} * \log(p_{ij})\right) \quad (2)$$

where,
N samples belong to M classes
y_ij, indicates whether sample i belongs to class j or not
p_ij, indicates the probability of sample i belonging to class j Confusion matrix metric gives a matrix as an output describing the accuracy of each of the predictions made by the model. It sorts out each prediction as True Positives (TP), where the prediction as well as observation both were true, True Negatives (TN), where the prediction as well as observation both were false, False Positives (FP) where the prediction was true but the observation was false, False Negatives (FN), where the prediction was false but the observation was true. Accuracy for a confusion matrix can be represented as per equation (3):

Accuracy=(TP +TN)/(N) - (3)

Where, N=total number of samples
Area under curve (AUC) uses a curve called receiver operating characteristic (ROC) curve to evaluate the performance of a model. ROC curve is a plot of specificity vs sensitivity of a model where:

Specificity=(FP)/(FP+TN) - (4)

and Sensitivity=(TP)/(FN+TP) - (5)

Area under the ROC curve is calculated and a model with high AUC is considered better performing.
F1 score is a harmonic mean of precision and recall, where:

Precision=(TP)/(TP+FP) - (6)

Recall=(TP)/(TP+FN) - (7)

F1 score=2*(1/precision+1/recall)$^{-1}$ - (8)

Mean absolute error is the average of the difference between the observations and the predictions.

$$\text{Mean absolute error} = \frac{1}{N}\sum_{j=1}^{N} |y_j - \hat{y}_j| \quad (9)$$

Where y_j is an observed value and ŷ_j is a predicted value.
Mean squared error is the average of the square of the difference between the original values and the predicted values.

$$\text{Mean squared error} = \frac{1}{N}\sum_{j=1}^{N} (y_j - \hat{y}_j)^2 \quad (10)$$

The rank allocator 406 then arranges the various permutations in the decreasing order of their respective accuracy scores and assigns a rank in that order to each permutation or a predetermined number of permutations. The preprocessing steps selector 407 selects the top-ranked or a specified number of the permutations of preprocessing parameters. If more than one permutation is selected, the selected permutations may be displayed as options to the user. The user may then select a suitable option for a more customized preprocessing based on the research requirements. The algorithm generator 408 then uses the top-ranked or user selected permutation of preprocessing parameters to generate an optimized preprocessing algorithm. The predictive model 409 then performs data analysis using the optimized preprocessing algorithm.

Figure 5:
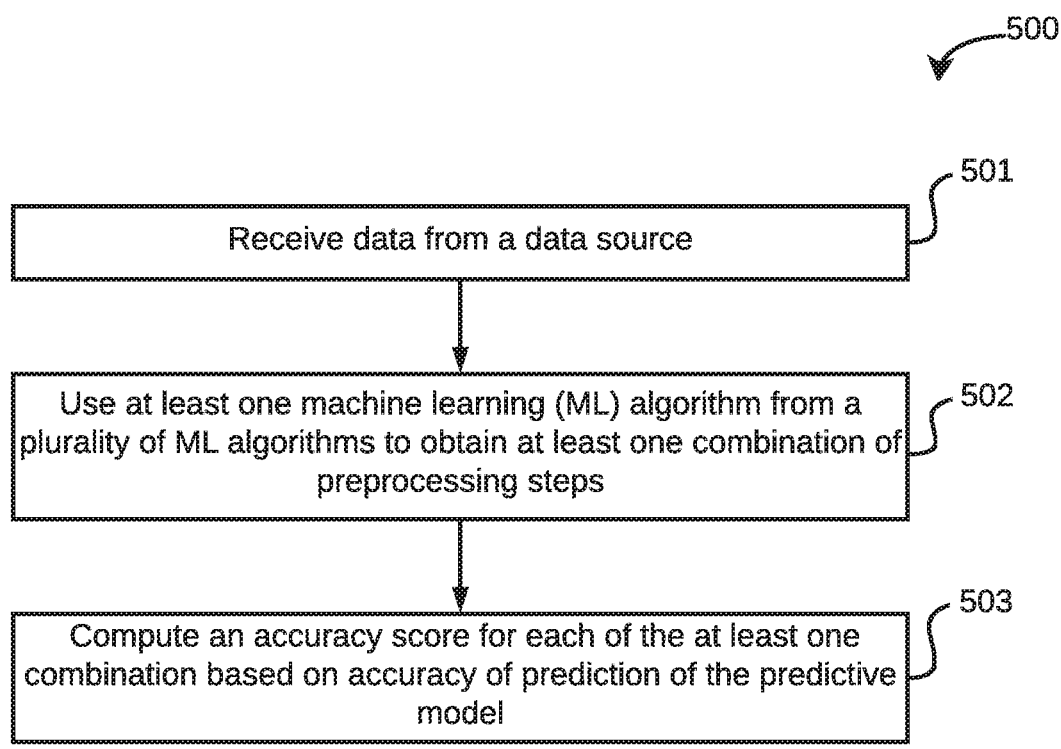
FIG. 5 is a flow diagram of an exemplary process for preprocessing biomedical data, in accordance with some embodiments of the present disclosure.

Referring now to FIG. 5, a flow diagram of an exemplary process 500 for preprocessing biomedical data, is illustrated, in accordance with some embodiments of the present disclosure. At step 501, the input data is received by the data receiver 402 from the data source 201. The data source 201 may be a part of the computer-readable medium 102 or one or more than one external device 105. The input data may be one or more than one large dataset. At step 502, at least one ML algorithm from a plurality of ML algorithms is applied, by the ML engine 403, on the preprocessing parameters to obtain at least one combination of preprocessing steps. The plurality of ML algorithms may include ML algorithms particularly created for biomedical data types, such as Magnetic Resonance Imaging (MRI), functional Magnetic Resonance Imaging (fMRI) data, an Electroencephalogram (EEG) data, an Electrocardiogram (EKG/ECG) data, a genetics data, a proteomics data, data from wearable devices, an Electronic Health Record (EHR) data, and Electronic Medical Record (EMR) data, Chemical Structures (SMILES, InCHI, SDF), Images (PNG, JPEG) including from histology or other applications of microscopy, and other healthcare and medical research related data options. At step 503, an accuracy score for each of the at least one combination of preprocessing steps is computed by the accuracy score calculator 405. The accuracy score may then be used as a basis for selecting a suitable combination of preprocessing parameters, leading to a suitable permutation of preprocessing steps.

Figure 6:
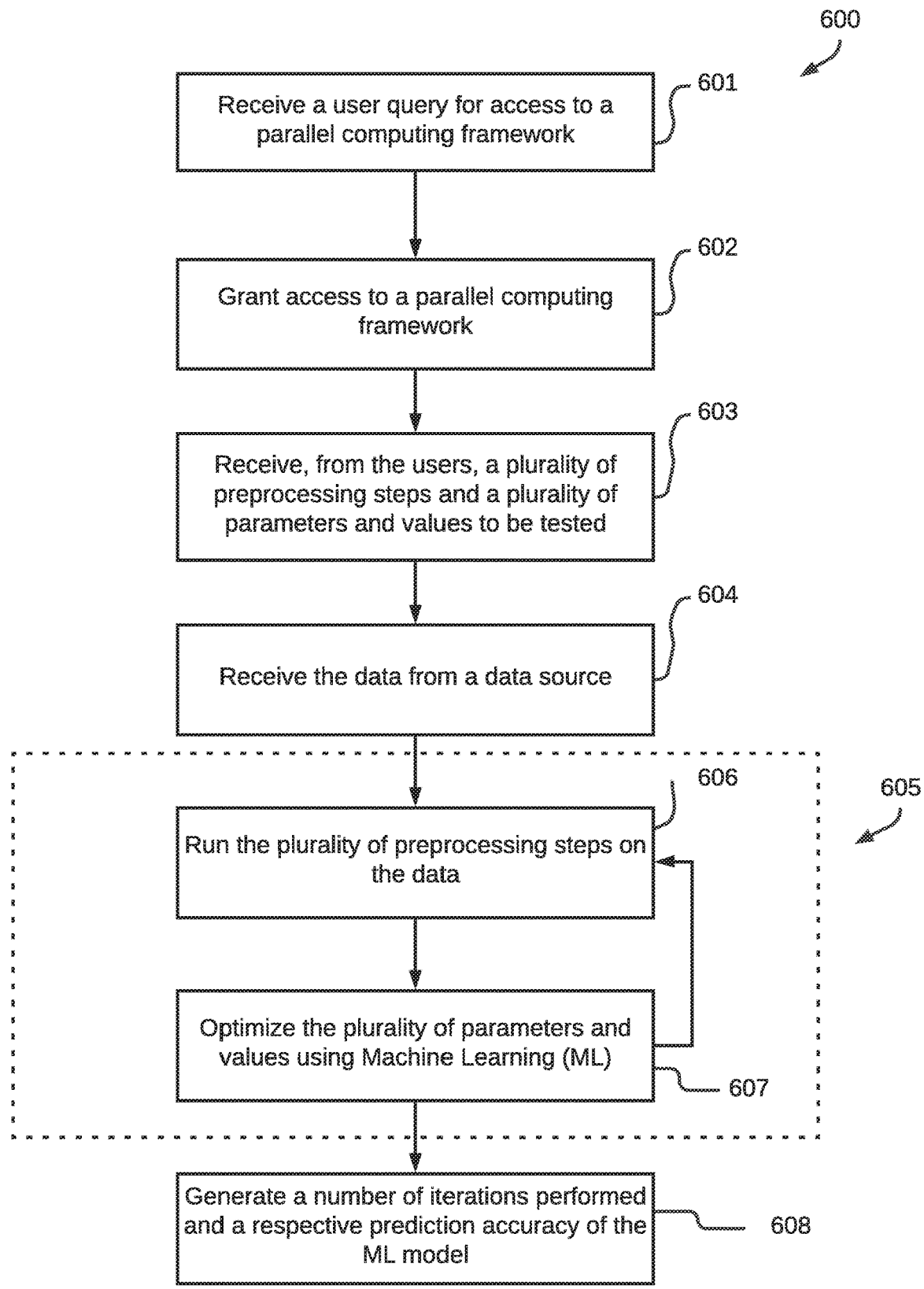
FIG. 6 is a flow diagram of an exemplary process of preprocessing biomedical data using the parallel computing network of FIG. 3, in accordance with some embodiments of the present disclosure.

Referring now to FIG. 6, a flow diagram of an exemplary process 600 of preprocessing biomedical data using the parallel computing network 300 of FIG. 3, is illustrated, in accordance with some embodiments of the present disclosure. An ML process 605 is also depicted within the process 600. As illustrated in the flow diagram, at step 601 of the process 600, the parallel computing network 300 may receive a user query from the users 312 for access to the parallel computing framework 305. Consequently, at step 602, the parallel computing network 300 may then grant access to the parallel computing framework 305.

At step 603, the parallel computing framework 305 may receive, from the users 312, a plurality of preprocessing steps and the plurality of parameters and values to be tested for each of the preprocessing steps. The users 312 may define a sequence of the preprocessing steps. At step 604, once the sequence of the preprocessing steps is defined, the parallel computing framework 305 may receive the data from the data source 201 via the API 302.

The ML process 605 for preprocessing the input data is depicted in the flow diagram. Within the ML process 605, at step 606, the ML engine 403, implemented by the parallel computing framework 305, may run the plurality of preprocessing steps on the data. At step 607, the ML engine 403, implemented by the parallel computing framework 305, may optimize the plurality of parameters and values for each of the preprocessing steps of step 606 using an ML algorithm. The ML process 605 may be an iterative process wherein the plurality of parameters and values may be used in the preprocessing steps of step 606 and tested, on a test sample of the input data, for the associated prediction accuracy by using the accuracy score calculator 405.

At step 608, the parallel computing framework 305 may generate a number of iterations performed, using the plurality of parameters and values of each of the preprocessing steps, and a respective prediction accuracy of each of the iterations.

(6) Data Integration and Feature Selection

Figure 7:
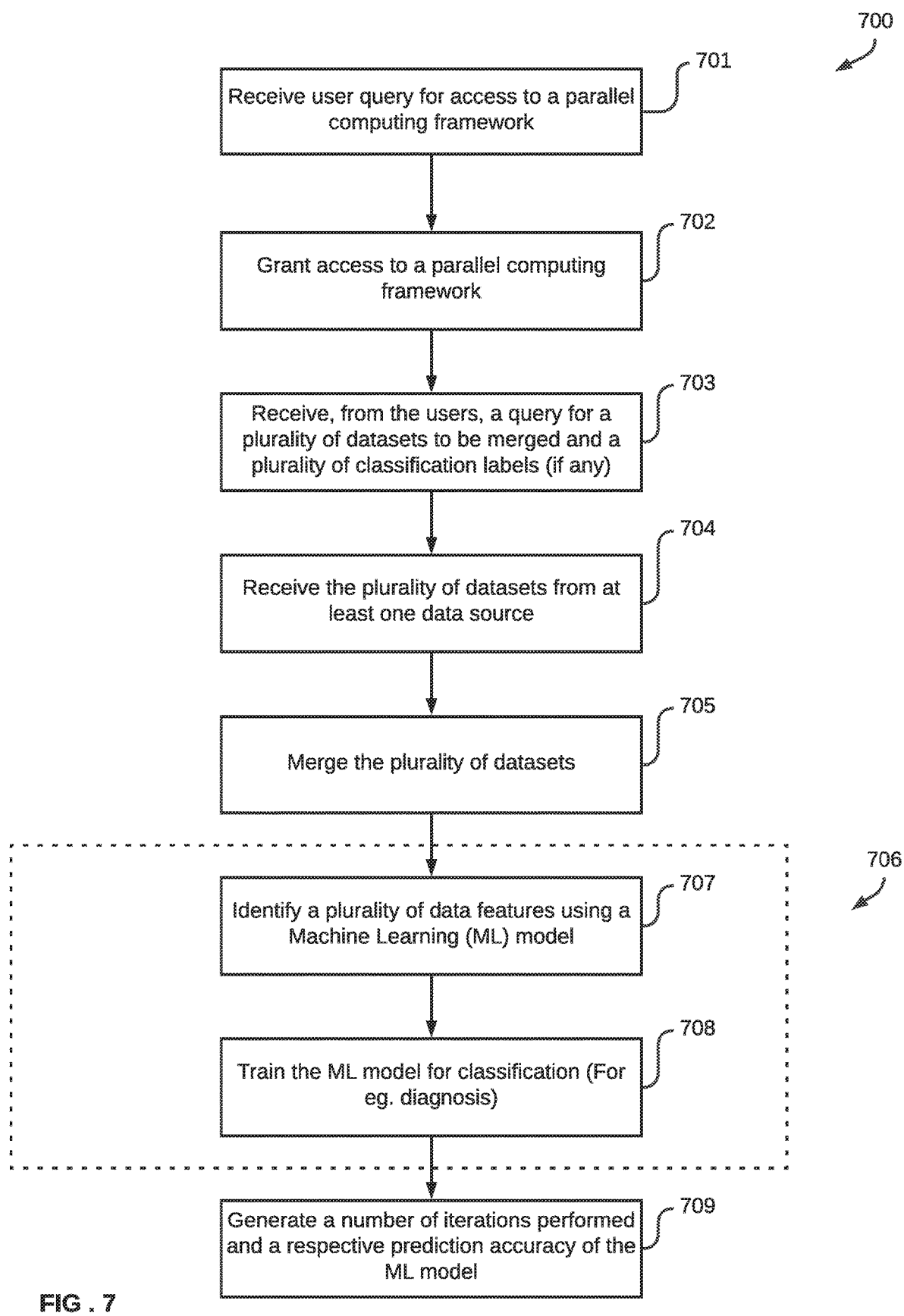
FIG. 7 is a flow diagram of an exemplary process of merging a plurality of datasets and selecting relevant features from the combined dataset using the parallel computing network of FIG. 3, in accordance with some embodiments of the present disclosure.

Referring now to FIG. 7, a flow diagram of an exemplary process 700 of merging a plurality of datasets and selecting relevant features from the combined dataset using the parallel computing network 300 of FIG. 3, is illustrated, in accordance with some embodiments of the present disclosure. A feature selection process 706 is also depicted within the process 700. As illustrated in the flow diagram, at step 701, the parallel computing network 300 may receive a user query from the users 312 for access to the parallel computing framework 305. Consequently, at step 702, the parallel computing network 300 may then grant access to the parallel computing framework 305.

At step 703, the parallel computing framework 305 may receive, from the users 312, a query for a plurality of datasets to be merged and a plurality of classification labels (if any). The plurality of datasets may have different data sources. At step 704, the parallel computing network 305 may receive the plurality of datasets from at least one data source. At step 705, the parallel computing network 305 may merge the plurality of datasets to give a combined dataset.

The feature selection process 706 for selecting the plurality of relevant features from the input data is depicted in the flow diagram. Within the feature selection process 706, at step 707, the parallel computing network 305 may identify a plurality of data features using a ML model. The ML model allows prediction of relevant data features, automating the feature selection process 706. At step 708, the parallel computing network 305 may train the ML model for classification problem such as diagnosis using the features obtained in step 707.

At step 709, the parallel computing network 305 may generate a number of iterations performed, using the features selected by the ML models of step 707, and a respective prediction accuracy of each of the ML models.

Figure 8:
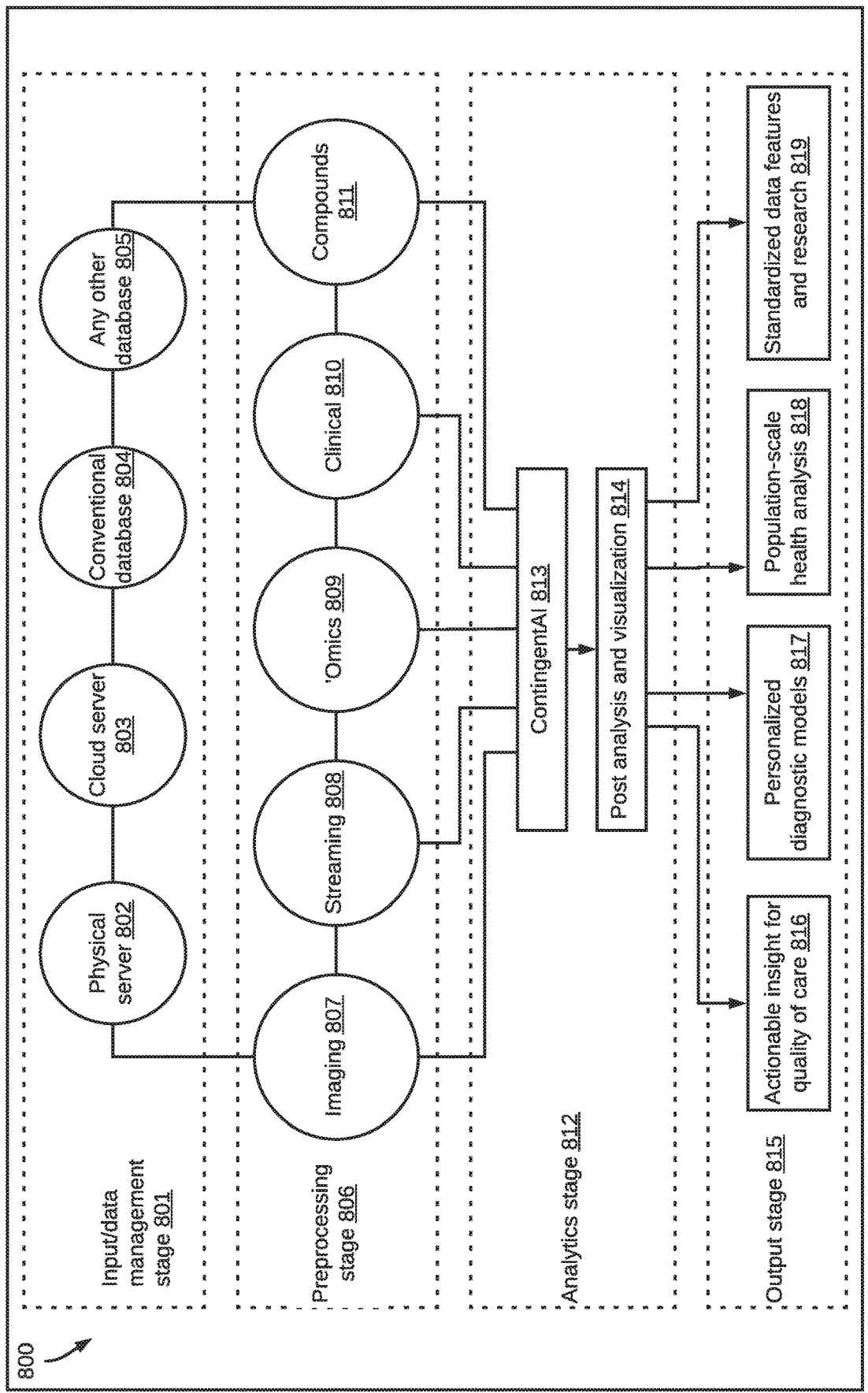
FIG. 8 is a block diagram depicting the examples of input sources and operations performed by the parallel computing network of FIG. 3, in accordance with some embodiments of the present disclosure.

Referring now to FIG. 8, a block diagram of the examples of input sources and operations 800 performed by the parallel computing network 300 of FIG. 3, is illustrated, in accordance with some embodiments of the present disclosure. The examples of input sources and operations 800 of the parallel computing network 300 include the examples of an input/data management stage 801, a preprocessing stage 806, an analytics stage 812, and an output stage 815.

The examples of the input/data management stage 801 include a physical server 802, a cloud server 803, a conventional database 804, and an any other database 805. The examples of the preprocessing stage 806 include an imaging 807, a streaming 808, an omics 809, a clinical 810, and compounds 811.

The analytics stage 812 is implemented by a ContingentAI 813, wherein the ContingentAI 813 is an artificial intelligence (AI)/ML based framework for big data analytics of biomedical data. The post analysis and visualization 814 of the results are sent as output to the output stage 815.

The examples of the output stage 815 include an actionable insight for quality of care 816, personalized diagnostic models 817, a population-scale health analysis 818, and a standardized data features and research 819.

(7) Variations on the Above Embodiments

It may be useful to arrange for the permutation generator 404 to generate ordered permutations based on previous rankings of configurations from the rank allocator 406.

It may be useful for the machine learning engine 403 to consider permutations in ranked order and to halt consideration when the accuracy score calculator 405 exceeds a specified threshold.

It may be useful to add pre-classified challenge data to the data source 201 in order to avoid certain sampling biases which may be present in the input data.

It may be useful to have the rank allocator 406 to weight accuracy scores 405 based on the accuracy of similar configurations against benchmarked data samples.

It may be useful for the machine learning algorithm 403 to evaluate the dependence or independence of choices in preprocessing 201 or feature selection 202. This evaluation may be used to reduce the total number of permutations to be examined.

It may be useful for the machine learning algorithm 403 to be seeded with rules or meta models for the selection of models 211 or hyperparameters 212 for the machine learning module 210.

It may be useful for the post analysis and visualization component 814 to present a plurality of results 213 as generated by different combinations of pre-processing steps and selections of features.

It may be useful for the post analysis and visualization component 814 to indicate areas of agreement or disagreement across models 210 generated by different combinations of pre-processing steps, feature selections, and model/hyperparameter settings.

It may be useful to arrange for the preprocessing engine 400 to accept pre-processing steps as defined by a particular programming language. The particular programming language can typically be a higher level programming language directed towards efficient coding of automated pre-processing tasks. It may be useful for the particular programming language to point out certain pre-processing tasks to be performed by the preprocessing engine.

(8) Computer Systems for Implementing Various Embodiments

Figure 9:
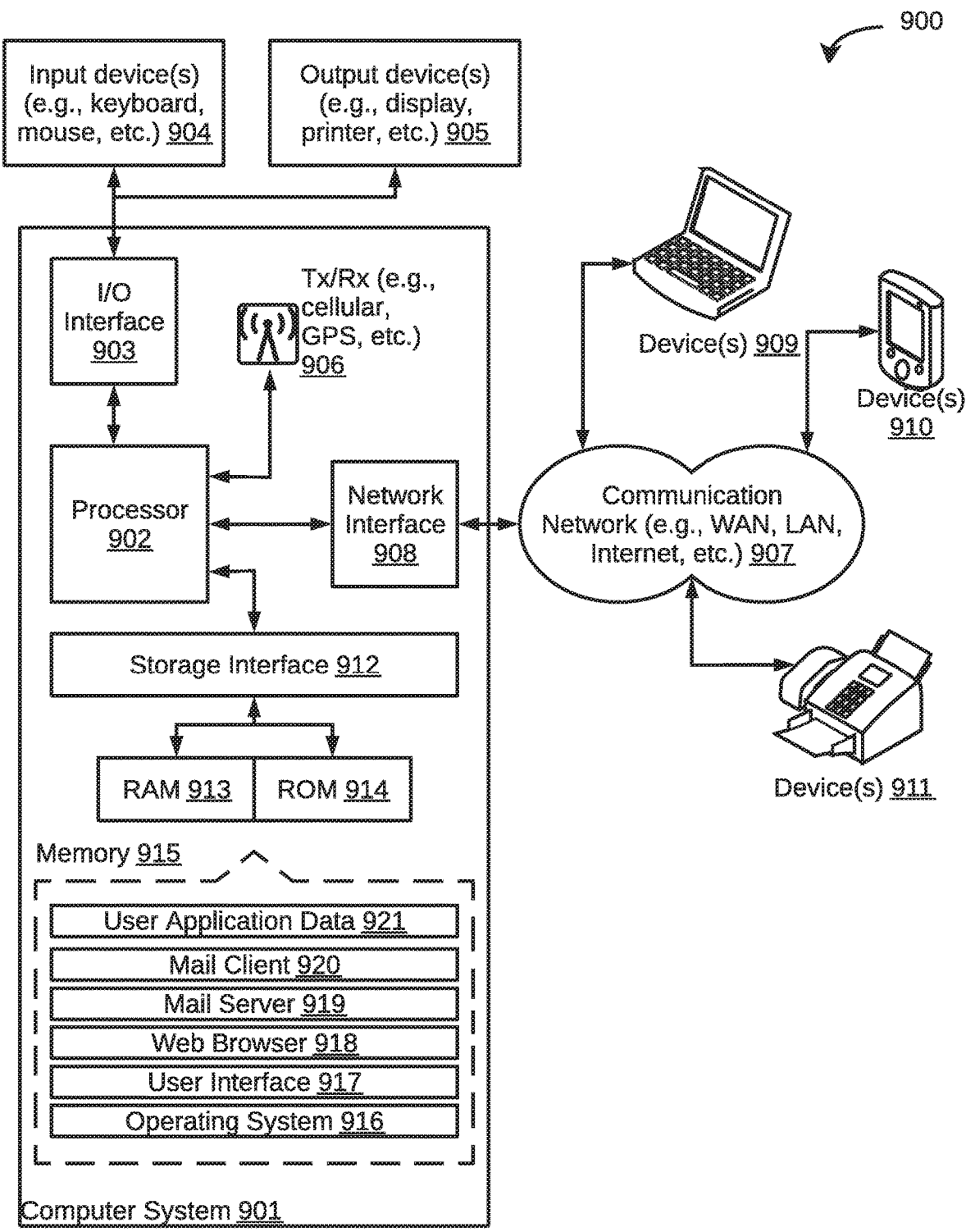
FIG. 9 is a block diagram of an exemplary computer system for implementing embodiments consistent with the present disclosure.

Referring now to FIG. 9, a block diagram of an exemplary computer system 901 for implementing embodiments consistent with the present disclosure is illustrated. Computer system 901 may include a central processing unit ("CPU" or "processor") 902. Processor 902 may include at least one data processor for executing program components for executing user- or system-generated requests. A user may include a person, a person using a device such as such as those included in this disclosure, or such a device itself. Processor 902 may include specialized processing units such as integrated system (bus) controllers, memory management control units, floating point units, graphics processing units, digital signal processing units, etc. Processor 902 may include a microprocessor, such as AMD® ATHLON® microprocessor, DURON® microprocessor OR OPTERON® microprocessor, ARM's application, embedded or secure processors, IBM® POWERPC®, INTEL'S CORE® processor, ITANIUM® processor, XEON® processor, CELERON® processor or other line of processors, etc. Processor 902 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), Graphical Processing Units (GPUs) (Nvidia, AMD, Asus, Intel, EVGA, and others), Tensor Processing Units (Google), etc.

Processor 902 may be disposed in communication with one or more input/output (I/O) devices via an I/O interface 903. I/O interface 903 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n /b/g/n/x, Bluetooth, cellular (e.g., code-division multiple access (CDMA), high-speed packet access (HSPA+), global system for mobile communications (GSM), long-term evolution (LTE), WiMax, or the like), etc.

Using I/O interface 903, computer system 901 may communicate with one or more I/O devices. For example, an input device 904 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc. An output device 905 may be a printer, fax machine, video display (e.g., cathode ray tube (CRT), liquid crystal display (LCD), light-emitting diode (LED), plasma, or the like), audio speaker, etc. In some embodiments, a transceiver 906 may be disposed in connection with processor 902. Transceiver 906 may facilitate various types of wireless transmission or reception. For example, transceiver 906 may include an antenna operatively connected to a transceiver chip (e.g., TEXAS® INSTRUMENTS WILINK WL1283® transceiver, BROADCOM® BCM4550IUB8® transceiver, INFINEON TECHNOLOGIES® X-GOLD 618-PMB9800® transceiver, or the like), providing IEEE 802.11 a/b/g/n, Bluetooth, FM, global positioning system (GPS), 2G/3G HSDPA/HSUPA communications, etc.

In some embodiments, processor 902 may be disposed in communication with a communication network 907 via a network interface 908. Network interface 908 may communicate with communication network 907. Network interface 616 may employ connection protocols including, without limitation, direct connect, Ethernet (e.g., twisted pair 50/500/5000 Base T), transmission control protocol/internet protocol (TCP/IP), token ring, IEEE 802.11 a/b/g/n/x, etc. Communication network 907 may include, without limitation, a direct interconnection, local area network (LAN), wide area network (WAN), wireless network (e.g., using Wireless Application Protocol), the Internet, etc. Using network interface 908 and communication network 907, computer system 901 may communicate with devices 909, 910, and 911. These devices may include, without limitation, personal computer(s), server(s), fax machines, printers, scanners, various mobile devices such as cellular telephones, smartphones (e.g., APPLE® IPHONE® smartphone, BLACKBERRY® smartphone, ANDROID® based phones, etc.), tablet computers, eBook readers (AMAZON® KINDLE® ereader, NOOK® tablet computer, etc.), laptop computers, notebooks, gaming consoles (MICROSOFT® XBOX® gaming console, NINTENDO® DS® gaming console, SONY® PLAYSTATION® gaming console, etc.), or the like. In some embodiments, computer system 901 may itself embody one or more of these devices.

In some embodiments, processor 902 may be disposed in communication with one or more memory devices (e.g., RAM 626, ROM 628, etc.) via a storage interface 912. Storage interface 912 may connect to memory 915 including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc.

Memory 915 may store a collection of program or database components, including, without limitation, an operating system 916, user interface application 917, web browser 918, mail server 919, mail client 920, user/application data 921 (e.g., any data variables or data records discussed in this disclosure), etc. Operating system 916 may facilitate resource management and operation of computer system 901. Examples of operating systems 916 include, without limitation, APPLE® MACINTOSH® OS X platform, UNIX platform, Unix-like system distributions (e.g., Berkeley Software Distribution (BSD), FreeBSD, NetBSD, OpenBSD, etc.), LINUX distributions (e.g., RED HAT®, UBUNTU®, KUBUNTU®, etc.), IBM® OS/2 platform, MICROSOFT® WINDOWS® platform (XP, Vista/7/8, etc.), APPLE® IOS® platform, GOOGLE® ANDROID® platform, BLACKBERRY® OS platform, or the like. User interface 917 may facilitate display, execution, interaction, manipulation, or operation of program components through textual or graphical facilities. For example, user interfaces may provide computer interaction interface elements on a display system operatively connected to computer system 901, such as cursors, icons, check boxes, menus, scrollers, windows, widgets, etc. Graphical user interfaces (GUIs) may be employed, including, without limitation, APPLE® Macintosh® operating systems' AQUA® platform, IBM® OS/2® platform, MICROSOFT® WINDOWS® platform (e.g., AERO® platform, METRO® platform, etc.), UNIX X-WINDOWS, web interface libraries (e.g., ACTIVEX® platform, JAVA® programming language, JAVASCRIPT® programming language, AJAX® programming language, HTML, ADOBE® FLASH® platform, etc.), or the like.

In some embodiments, computer system 901 may implement a web browser 918 stored program component. Web browser 918 may be a hypertext viewing application, such as MICROSOFT® INTERNET EXPLORER® web browser, GOOGLE® CHROME® web browser, MOZILLA® FIREFOX® web browser, APPLE® SAFARI® web browser, etc. Secure web browsing may be provided using HTTPS (secure hypertext transport protocol), secure sockets layer (SSL), Transport Layer Security (TLS), etc. Web browsers may utilize facilities such as AJAX, DHTML, ADOBE® FLASH® platform, JAVASCRIPT® programming language, JAVA® programming language, application programming interfaces (APIs), etc. In some embodiments, computer system 901 may implement a mail server 919 stored program component. Mail server 919 may be an Internet mail server such as MICROSOFT® EXCHANGE® mail server, or the like. Mail server 638 may utilize facilities such as ASP, ActiveX, ANSI C++/C#, MICROSOFT.NET® programming language, CGI scripts, JAVA® programming language, JAVASCRIPT® programming language, PERL® programming language, PHP® programming language, PYTHON® programming language, WebObjects, etc. Mail server 919 may utilize communication protocols such as internet message access protocol (IMAP), messaging application programming interface (MAPI), Microsoft Exchange, post office protocol (POP), simple mail transfer protocol (SMTP), or the like. In some embodiments, computer system 901 may implement a mail client 920 stored program component. Mail client 920 may be a mail viewing application, such as APPLE MAIL® mail client, MICROSOFT ENTOURAGE® mail client, MICROSOFT OUTLOOK® mail client, MOZILLA THUNDERBIRD® mail client, etc.

In some embodiments, computer system 901 may store user/application data 921, such as the data, variables, records, etc. as described in this disclosure. Such databases may be implemented as fault-tolerant, relational, scalable, secure databases such as ORACLE® database OR SYBASE® database. Alternatively, such databases may be implemented using standardized data structures, such as an array, hash, linked list, struct, structured text file (e.g., XML), table, or as object-oriented databases (e.g., using OBJECTSTORE® object database, POET® object database, ZOPE® object database, etc.). Such databases may be consolidated or distributed, sometimes among the various computer systems discussed above in this disclosure. It is to be understood that the structure and operation of the any computer or database component may be combined, consolidated, or distributed in any working combination.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

As will be appreciated by those skilled in the art, the techniques described in the various embodiments discussed above are not routine, or conventional, or well understood in the art. The techniques discussed above provide for preprocessing biomedical data for a predictive model using an ML algorithm. The ML algorithm uses different permutations of preprocessing parameters to generate an optimized preprocessing algorithm. The preprocessing of biomedical data is implemented via an AI/ML-based framework for big data analytics of biomedical data. The AI/ML-based framework also provides for an iterative feature selection module, a capability for integration of various datasets, and a parallel computing network. Various datasets are integrated, and the features are then selected for the combined dataset. The feature selection is optimized by another ML algorithm. The parallel computing network allows a plurality of users to work together on a same input data and can also be used to implement containerized deployment to execute the analytics at a faster rate.

The specification has described a method and a system for preprocessing biomedical data for a predictive model. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for preprocessing biomedical data for a predictive model, the method comprising:
   receiving data from a data source;
   using at least one machine learning (ML) algorithm from a plurality of ML algorithms to generate multiple permutations of preprocessing steps, the preprocessing steps having parameters and values;
   computing an accuracy score for each of the multiple permutations of the preprocessing steps based on accuracy of prediction of the predictive model; and
   optimizing the parameters and the values of each of the preprocessing steps, and an order in which the steps are performed.

2. The method of claim 1, wherein the data source comprises at least one of a local data storage, a database, and a cloud data storage.

3. The method of claim 1, wherein the data is one of Magnetic Resonance Imaging (MRI) data, functional Magnetic Resonance Imaging (fMRI) data, Electroencephalogram (EEG) data, Electrocardiogram (EKG/ECG) data, genetics data, proteomics data, data from wearable devices, Electronic Health Record (EHR) data, Electronic Medical Record (EMR) data, Chemical structure data, Images (PNG, JPEG), including from pathology or other applications of microscopy, and other healthcare and medical research or healthcare related data.

4. The method of claim 1, wherein the method further comprises selecting one combination of preprocessing steps from the at least one plurality of combination of preprocessing steps, wherein the accuracy score of the selected at least one combination of preprocessing steps is greater than a predefined threshold rank.

5. The method of claim 1, wherein the accuracy score is calculated by an evaluation metric, and wherein the evaluation metric comprises at least one of a classification accuracy, a logarithmic loss, a confusion matrix, an area under curve (AUC), an F1 score, a mean absolute error, a mean squared error, or a performance evaluation metric.

6. The method of claim 1, further comprising distributing the plurality of ML algorithms over a cluster of computers or processors in a single computer.

7. The method of claim 1, wherein the preprocessing steps comprise at least one of a pixel threshold determination, linear regression computation, non-linear regression computation, volume threshold determination, or a smoothing method.

8. The method of claim 1, further comprising using the selected at least one combination of preprocessing steps to generate data for the predictive model.

9. The method of claim 1, further comprising:
detecting a bias in the data, wherein the bias comprises at least one of a selection bias, a reporting bias, a recall bias, an exclusion bias, an information bias, or a statistical bias; and
correcting the bias using at least one suitable preprocessing algorithm.

10. The method of claim 1, further comprising visualizing an output by using one of a Seaborn package, a Matplotlib package, or a data visualization package.

11. A system for preprocessing biomedical data for a predictive model, the system comprising:
an iterative data preprocessing device that includes at least one processor and a computer-readable medium storing instructions that, when executed by the at least one processor, cause the at least one processor to perform at least the following operations:
receiving data from a data source;
using at least one ML algorithm from a plurality of ML algorithms to generate multiple permutations of preprocessing steps, the preprocessing steps having parameters and values;
computing an accuracy score for each of the multiple permutations of the preprocessing steps based on accuracy of prediction of the predictive model; and
optimizing the parameters and the values of each of the preprocessing steps, and an order in which the steps are performed.

12. The system of claim 11, wherein the data source comprises at least one of a local data storage, a database, and a cloud data storage.

13. The system of claim 11, wherein the data is one of Magnetic Resonance Imaging (MRI) data, functional Magnetic Resonance Imaging (fMRI) data, Electroencephalogram (EEG) data, Electrocardiogram (EKG/ECG) data, genetics data, proteomics data, data from wearable devices, Electronic Health Record (EHR) data, Electronic Medical Record (EMR) data, Chemical structure data, Images (PNG, JPEG), including from pathology or other applications of microscopy, and other healthcare and medical research or healthcare related data.

14. The system of claim 11, wherein the system further comprises selecting one combination of preprocessing steps from the at least one plurality of combination of preprocessing steps, wherein the accuracy score of the selected at least one combination of preprocessing steps is greater than a predefined threshold rank.

15. The system of claim 11, wherein the accuracy score is calculated by an evaluation metric, and wherein the evaluation metric comprises a classification accuracy, a logarithmic loss, a confusion matrix, an area under curve (AUC), an F1 score, a mean absolute error, a mean squared error, or a performance evaluation metric.

16. The system of claim 11, wherein the operations further comprise distributing the plurality of ML algorithms over a cluster of computers.

17. The system of claim 11 wherein the preprocessing steps comprise at least one of a pixel threshold determination, linear regression computation, non-linear regression computation, volume threshold determination, or a smoothing method.

18. The system of claim 14, wherein the operations further comprise using the selected at least one combination of preprocessing steps to generate data for the predictive model.

19. The system of claim 11, wherein the operations further comprise:
detecting a bias in the data, wherein the bias comprises at least one of a selection bias, a reporting bias, a recall bias, an exclusion bias, an information bias, or a statistical bias; and
correcting the bias using at least one suitable preprocessing algorithm.

20. The system of claim 11, wherein a user specifies a sequence of operations, a criteria for a success, and a deployment of pre- and post-processing using a graphic user interface (GUI).

21. The system of claim 11, wherein the operations further comprise visualizing an output by using one of a Seaborn package, a Matplotlib package, or a data visualization packages.

* * * * *